United States Patent
Wang et al.

(10) Patent No.: US 10,556,899 B2
(45) Date of Patent: Feb. 11, 2020

(54) METHOD FOR PREPARING MARAVIROC

(71) Applicant: SCI Pharmtech, Inc., Taoyuan (TW)

(72) Inventors: Heng-Yen Wang, Taoyuan (TW); Chen-Yi Kao, Taoyuan (TW)

(73) Assignee: SCI Pharmtech, Inc., Taoyuan (TW)

( * ) Notice: Subject to any disclaimer, the term of this patent is extended or adjusted under 35 U.S.C. 154(b) by 0 days.

(21) Appl. No.: 16/257,987

(22) Filed: Jan. 25, 2019

(65) Prior Publication Data

US 2019/0248782 A1  Aug. 15, 2019

Related U.S. Application Data

(60) Provisional application No. 62/628,663, filed on Feb. 9, 2018.

(51) Int. Cl.
*C07D 451/02* (2006.01)

(52) U.S. Cl.
CPC .................. *C07D 451/02* (2013.01)

(58) Field of Classification Search
CPC .................................. C07D 451/02
USPC ........................................ 546/112
See application file for complete search history.

(56) References Cited

U.S. PATENT DOCUMENTS

| | | | | |
|---|---|---|---|---|
| 6,667,314 B2 * | 12/2003 | Perros | ............... | A61K 31/4196 514/304 |
| 7,294,636 B2 * | 11/2007 | Cumming | ............ | C07D 401/04 514/304 |
| 7,615,555 B2 * | 11/2009 | Faull | .................... | C07D 401/14 514/253.04 |
| 7,932,235 B2 * | 4/2011 | Tung | .................... | C07D 451/04 514/304 |
| 8,410,094 B2 * | 4/2013 | Long | .................... | C07D 451/04 514/233.2 |
| 8,779,143 B2 * | 7/2014 | Reddy | .................... | A61K 31/46 546/125 |
| 2008/0146605 A1 * | 6/2008 | Gant | .................... | C07D 451/02 514/299 |

FOREIGN PATENT DOCUMENTS

| | | | |
|---|---|---|---|
| CN | 102584814 | * | 7/2012 |
| CN | 102766141 | * | 11/2012 |
| CN | 104860946 | * | 8/2015 |

OTHER PUBLICATIONS

Ahman; Org. Process Res. Dev. 2008, 12, 1104-1113. (Year: 2008).*
Anderson; Chapter 4 in "Practical Process Research and Development", Academic Press, 2000, pp. 81-111. (Year: 2000).*
Haycock-Lewandowski; Org. Process Res. Dev. 2008, 12, 1094-1103. (Year: 2008).*
Lee; Dalton Trans., 2014, 43, 8888-8893, with supporting information. (Year: 2014).*
Price; Synlett 2005, 1133-1134. (Year: 2005).*
Ulrich; Chapter 3 in "The Chemistry of Imidoyl Halides", Plenum Press, 1968, pp. 55-112. (Year: 1968).*
Zhao; Adv. Synth. Catal. 2010, 352, 2291-2298. (Year: 2010).*

* cited by examiner

*Primary Examiner* — Daniel R Carcanague
(74) *Attorney, Agent, or Firm* — Mintz Levin Cohn Ferris Glovsky and Popeo, P.C.; Peter F. Corless; Joohee Lee

(57) ABSTRACT

Provided is a method for preparing a tropane derivative, maraviroc, including reacting a compound of formula (II) with a compound of formula (I), wherein the compound of formula (II) is prepared by the steps of acetylation of a compound of formula (III), activation and substitution of a compound of formula (IV) by a chlorination agent, cyclization of a compound of formula (V), and debenzylation of a compound of formula (VI) by hydrogenation. Hence, the present disclosure provides a method for preparing maraviroc with good yield and simple operation.

18 Claims, No Drawings

METHOD FOR PREPARING MARAVIROC

This Application claims the benefit of U.S. Provisional Application 62/628,663 filed on Feb. 9, 2018. The entire contents of these applications are incorporated herein by reference in their entirety.

BACKGROUND

1. Technical Field

The present disclosure relates to methods for preparing tropane derivatives, particularly to methods for preparing maraviroc.

2. Description of Associated Art

Maraviroc (Selzentry®), i.e., 4,4-difluoro-N-{(1S)-3-[exo-3-(3-isopropyl-5-methyl-4H-1,2,4-triazol-4-yl)-8-azabicyclo[3.2.1]oct-8-yl]-1-phenylpropyl}cyclohexanecarboxamide, is a CCR5 modulator used for treatment of AIDS. U.S. Pat. Nos. 6,667,314 and 7,368,460 disclose the method for preparation of Maraviroc. The key starting compounds are 4,4-difluorocyclohexanecarboxylic acid, methyl (S)-3-amino-3-phenylpropanoate and (1R,5S)-3-(3-isopropyl-5-methyl-4H-1,2,4-triazol-4-yl)-8-azabicyclo[3.2.1]octane. Among the three starting compounds, the last one is the most complicated in commercial production. As demonstrated in scheme 1 of U.S. Pat. No. 6,667,314 (shown below), six steps are required to prepare the product, and the total yield is around 6%. Therefore, the process is costly and a lot of wastes would be generated. Moreover, the most critical step in the process is hydrazine mediated cyclization, which gave the lowest yield among all the steps at 30%.

Scheme 1. The process of U.S. Patent No. 6,667,314

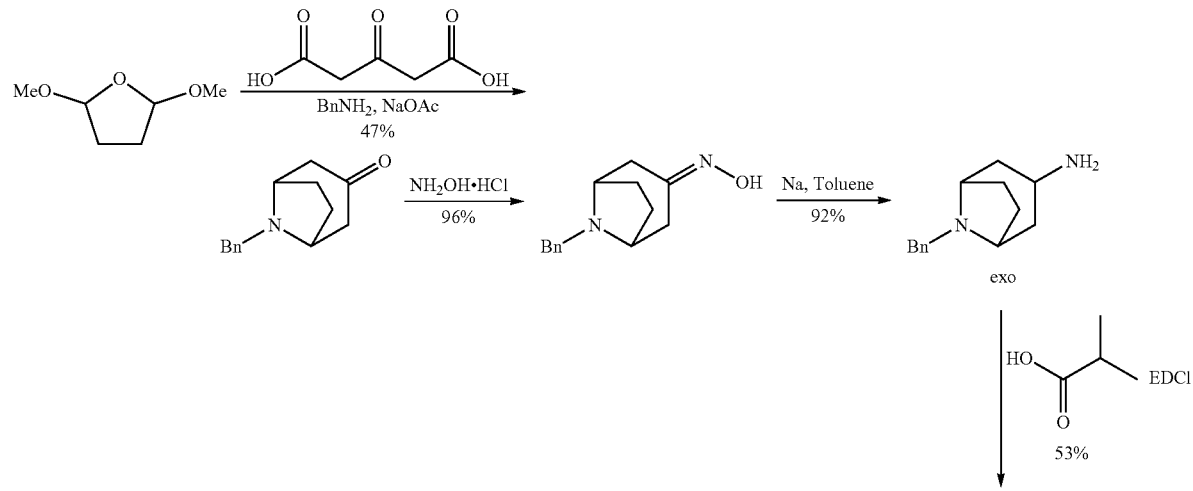

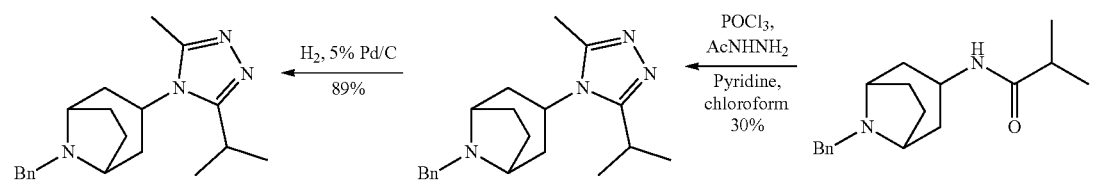

Subsequently, another synthesis process has been reported in Organic Process Research & Development, 2008, 12, 1094-1103, where phosphorus pentachloride is used to replace the phosphorous oxychloride in the hydrazine mediated cyclization step, and is able to increase the yield substantially. However, the phosphorus pentachloride used as the replacement is very difficult to handle in massive production because it aggregates easily and turns to fuming hydrochloride when contacted moisture. Moreover, phosphorus pentachloride belongs to class III material in Organization for Prohibition of Chemical Weapons (OPCW), and its use is therefore strictly regulated.

Accordingly, a feasible process with good yield and simple operation in large quantity production is still needed.

SUMMARY

In view of the foregoing, the present disclosure provides a method for preparing maraviroc, comprising a step of reacting of an intermediate compound represented by formula (I) below,

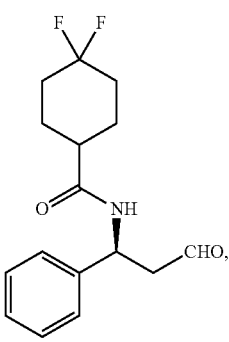
(I)

with an intermediate compound of secondary amine represented by formula (II) below,

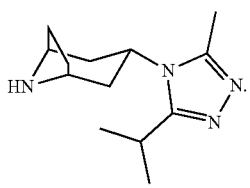
(II)

In an embodiment of the present disclosure, the method further comprises preparation of the intermediate compound represented by formula (II), comprising:

acetylating an intermediate compound represented by formula (III) below,

(III)

to obtain an intermediate compound represented by formula (IV) below,

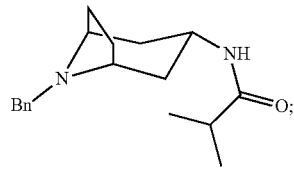
(IV)

reacting the intermediate compound represented by formula (IV) with a chlorination agent to obtain an intermediate compound represented by formula (V) below,

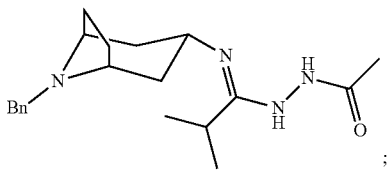
(V)

cyclizing the intermediate compound represented by formula (V) to obtain an intermediate compound represented by formula (VI) below,

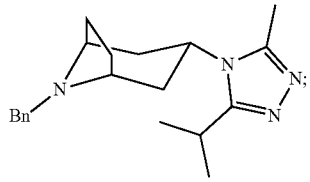
(VI)

debenzylating the intermediate compound represented by formula (VI) by hydrogenation to obtain the intermediate compound represented by formula (II).

In an embodiment of the present disclosure, the step of reacting the intermediate compound represented by formula (IV) with the chlorination agent comprises activation and substitution of the intermediate compound represented by formula (IV). In another embodiment of the present disclosure, the substitution is carried out in the presence of a base at low temperature.

In an embodiment of the present disclosure, the low temperature is in a range from −10° C. to 25° C. In another embodiment of the present disclosure, the low temperature is in a range from 0° C. to 5° C.

In an embodiment of the present disclosure, the base is a tertiary amine selected from the group consisting of triethylamine (TEA), N,N-diisopropylethylamine (DIPEA), 1,8-diazabicyclo[5.4.0]undec-7-ene (DBU), 1,4-diazabicyclo[2.2.2]octane (DABCO), 1,5-diazabicyclo[4.3.0]non-5-ene (DBN), N-methylmorpholine and pyridine. In an embodiment of the present disclosure, the base is pyridine. In another embodiment of the present disclosure, the equivalent of pyridine is 2.2 to 8.8. In still another embodiment of the present disclosure, the equivalent of pyridine is around 4.4.

In an embodiment of the present disclosure, the chlorination agent is $SOCl_2$, $POCl_3$, $PCl_3$ or $PCl_5$. In one embodiment of the present disclosure, the chlorination agent is $SOCl_2$. In another embodiment of the present disclosure, the equivalent of SOCl$_2$ is 1.3 to 1.7. In still another embodiment of the present disclosure, the equivalent of SOCl$_2$ is around 1.5.

In an embodiment of the present disclosure, the step of reacting the intermediate compound represented by formula (IV) with the chlorination agent is carried out in the presence of a reaction solvent. In one embodiment of the present disclosure, the reaction solvent is an aprotic solvent including, but not limited to, dichloromethane, acetonitrile, tetrahydrofuran, ethyl acetate and dimethyl formamide. In one embodiment, the reaction solvent is acetonitrile.

In an embodiment of the present disclosure, the weight ratio of the intermediate compound represented by formula (IV) to the aprotic solvent is from 1:4 to 1:12. In another embodiment of the present disclosure, the weight ratio of the intermediate compound represented by formula (IV) to the aprotic solvent is about 1:8.

DETAILED DESCRIPTION OF THE EMBODIMENTS

The following illustrative embodiments are provided to illustrate the disclosure of the present specification. These and other aspects and effects can be obviously understood by those skilled in the art after reading the present disclosure. The present disclosure can also be performed or applied by other different embodiments. The details of the specification may be on the basis of different points and applications, and numerous modifications and variations can be devised without departing from the spirit of the present disclosure.

In an embodiment of the present disclosure, thionyl chloride is used to replace phosphorus pentachloride for at least the following reasons: (a) more user-friendly operating environment, especially in massive production, is provided; (b) thionyl chloride is not under regulation by OPCW; and (c) less waste would be generated since phosphorus pentachloride forms a stronger acid as compared with thionyl chloride in the same equivalent.

The yields and accessibility in operation are more superior in the present disclosure in comparison with existing prior art.

The following are specific embodiments further demonstrating the efficacy of the current disclosure, but are not to limit the scope of the present disclosure.

EXAMPLE

Example 1: Preparation of Compound (III)

8-benzyl-8-azabicyclo [3.2.1] octan-3-one oxime (92.5 g, 0.40 mole) and sodium (111 g, 4.83 mole) were mixed in toluene (1110 g) at ambient temperature under inert atmosphere. The mixture was heated to reflux before adding 1-butanol (1181 g, 15.93 mole). The reaction mixture was allowed to stir at reflux for a half hour. Second portion of Na (21 g, 0.91 mole) was then added to the reaction mixture, and it was allowed to reflux for 2 hours to obtain crude compound (III) with purity of 85.7% by ultra-performance liquid chromatography (UPLC). Compound (III) was converted to compound (IV) without further purification.

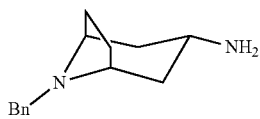

(III)

Example 2: Preparation of Compound (IV)

Crude compound (III) as prepared in Example 1 was quenched by water (1187 g) before adding isobutyryl chloride (55.8 g, 0.52 mole) at 0° C., and the reaction was allowed to stir for 1 hour before adding an additional portion of isobutyryl chloride (20.0 g, 0.18 mole). The organic layer was separated from an aqua layer, and it was washed twice with water (516 g and 490 g, respectively) to obtain crude compound (IV) with purity of 85.7% by UPLC and reaction yield of 89.3% from 8-benzyl-8-azabicyclo [3.2.1] octan-3-one oxime. The crude compound (IV) in the organic layer was then reduced at 40 torr/70° C. and combined with other batches to obtain a 140 g residue. Toluene (340 g) was added to the residue to obtain a total weight in 480 g. The mixture was heated up to 70° C. and cooled down slowly to room temperature. Heptane (100 g) was added to the mixture at ambient temperature and cooled down to 0° C. before filtration. The wet cake (138.3 g) was obtained after filtration, and compound (IV) of the dry cake (120.2 g) was obtained after drying (purity 99.9% by UPLC).

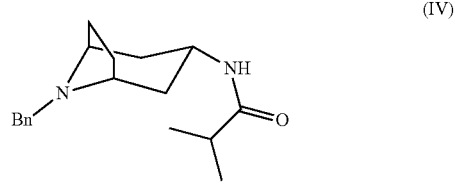 [SMILES: CC(C)C(=O)NC1CC2CCC(C1)N2Cc1ccccc1]

(IV)

Example 3: Preparation of Compound (VI)

Compound (IV) (57.2 g, 0.20 mole) as prepared in Example 2 and pyridine (69.5 g, 0.88 mole) were diluted with acetonitrile (419 g) under inert atmosphere. The mixture was cooled down to 0° C. and added with thionyl chloride (35.7 g, 0.30 mole) and then stirred for 1 hour. The reaction mixture was transferred to a 2-L round bottom flask charging with a 22% hydrazine acetonitrile solution (270 g). The reaction mixture was allowed to stir at 0° C. for 30 minutes followed by warming up to ambient temperature, and then it was allowed to stir further for another 30 minutes. Water (405.0 g) was added to the reaction flask, and the reaction mixture was basified to pH=11.5 by 45% NaOH$_{(aq)}$, followed by adding toluene (501.5 g). The organic layer was separated from an aqua layer, and it was reduced at 40 torr/70° C. to obtain crude compound (V).

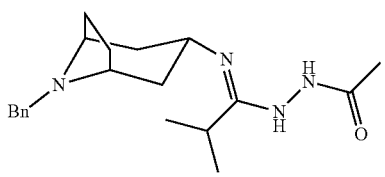

(V)

The crude compound (V) was stripped with 150 g toluene twice and diluted by isopropyl alcohol (IPA) (383 g). 98% acetic acid (HOAc; 18.2 g, 0.3 mol, 1.5 equivalent (eq.)) was added into the mixture and heated to reflux for a half hour. IPA was removed from the reaction mixture by simple distillation, and the residue was stripped with 200 g water twice. Residues were diluted with 32% HCl (70 g) and water to obtain a total weight in 500 g followed by heating at outside temperature (OT)=100° C. for 15 hours. The mixture was cooled down to room temperature and basified to a pH value around 11 with 45% NaOH before adding toluene (302 g). The organic layer was separated from an aqua layer and washed by 100 g water for three times, and it was reduced at 40 torr/70° C. to obtain a 120 g residue. Toluene was added to the residue to obtain a total weight of 165 g. Heptane (110 g) was added to the mixture at ambient temperature and cooled down to 0° C. before filtration. The wet cake (53.8 g) was obtained after filtration, and it was re-slurred in heptane (90 g). The wet cake (49.4 g) was obtained after filtration, and compound (VI) of the dry cake was obtained after drying (49.0 g; 75.6% yield; purity 99.7% by UPLC).

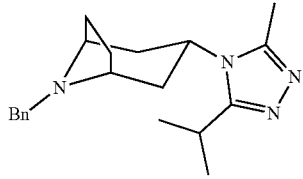

(VI)

Example 4: Preparation of Compound (II)

Compound (VI) (8.0 g, 0.025 mol) as prepared in Example 3 and wet 5% Pd/C (0.96 g, 12 wt. %) were charged in the hydrogenation vessel and diluted with MeOH (80 g). The reaction mixture of compound (VI) was heated up to 60° C. under 5 atmospheric (atm) pressure of $H_2$ for a half hour followed by addition of a second portion of wet 5% Pd/C (0.48 g, 6 wt. %). Further, the reaction mixture was heated up to 60° C. under 5 atm pressure of $H_2$ until compound (VI) was undetectable. The reaction mixture was then cooled down to ambient temperature, and the Pd/C was filtered off to obtain crude compound (II).

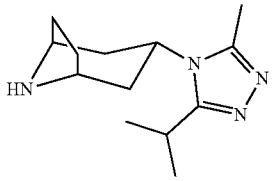

(II)

Example 5: Preparation of Compound (I)

Compound (I) was prepared through oxidation of (S)-4,4-difluoro-N-(3-hydroxy-1-phenylpropyl)cyclohexanecarboxamide, which was made from the reduction of (3S)-3-[(4,4-difluorocyclohexanecarbonyl)amino]-3-phenylpropanoate.

Briefly, 4,4-difluorocyclohexanedcarboxylic acid (16.4 g), dichloromethane (DCM; 60 g), and $SOCl_2$ (11.8 g) were mixed and heated at reflux for 15 hours to form solution A. (S)-3-amino-3-phenyl propionic acid methylester HCl (21.5 g), $H_2O$ (65 g), and $NaHCO_3$ (21 g) were mixed followed by cooling down the solution with an ice bath to form solution B. Solution A was transferred into solution B, and the reaction mixture was subjected to stir further for 30 min. The organic phase was collected by phase separation and concentrated under reduced pressure. Methyl (3S)-3-[(4,4-difluorocyclohexanecarbonyl)amino]-3-phenylpropanoate was crystallized from MeOH/$H_2O$ with 91% yield (2.9 g).

Methyl (3S)-3-[(4,4-difluorocyclohexanecarbonyl)amino]-3-phenylpropanoate (16 g), $NaBH_4$ (2.5 g), and tetrahydrofuran (THF, 33 g) were mixed and heated to 40° C. followed by the addition of MeOH (8 g). The reaction mixture was subjected to stirring for 3 hours before quenching with $H_2O$ (1 g), and then it was concentrated under reduced pressure. The crude residue was stripped with MeOH (33 g) twice and crystallized from MeOH/$H_2O$ to obtain (S)-4,4-difluoro-N-(3-hydroxy-1-phenylpropyl)cyclohexanecarboxamide with yield of 96% (14 g).

(S)-4,4-difluoro-N-(3-hydroxy-1-phenylpropyl)cyclohexanecarboxamide (5 g), ethyl acetate (EA; 70 g), NaBr (1.7 g), $NaHCO_3$ (1.9 g), $H_2O$ (70 g), and (2,2,6,6-tetramethylpiperidin-1-yl)oxyl (0.03 g) were mixed and cooled down with an ice bath before adding NaOCl (11 g). The mixture was then subjected to reaction for 30 min at 0° C. The organic phase was collected by phase separation and concentrated under reduced pressure. Crystallization with toluene gave compound (I) with 91% yield (4 g).

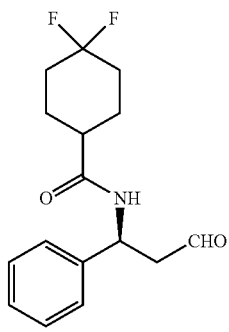

(I)

Example 6: Preparation of Maraviroc

Compound (I) (3.09 g) as prepared in Example 5, compound (II) (2.34 g) as prepared in Example 4, and THF (30 g) were mixed in a round bottom flask. After the mixture was cooled in an ice bath and reacted for 10 min, HOAc (1.5 g) was added into the mixture and reacted for another 10 min. Subsequently, $NaBH(OAc)_2$ (3.2 g) was added into the reaction mixture to reduce intermediate to crude product. The whole reaction mixture was quenched with 15% NaOH to pH>10. The organic phase was collected by phase separation, and concentrated under reduced pressure. Maraviroc (4.6 g) in a form of white powder was obtained from the concentrate by crystallization with EA.

The disclosure has been described using exemplary embodiments. However, it should be understood that the scope of the disclosure is not limited to the disclosed embodiments. On the contrary, it is intended to cover various modifications and similar rearrangements. The scope of the claims therefore should be accorded the broadest interpretation so as to encompass all such modifications and similar rearrangements.

The invention claimed is:

1. A method for preparation of maraviroc, comprising reacting an intermediate compound represented by formula (IV) below,

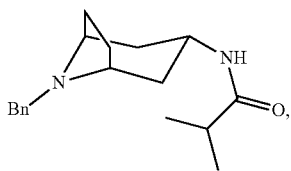

(IV)

with a chlorination agent to obtain an intermediate compound represented by formula (V) below,

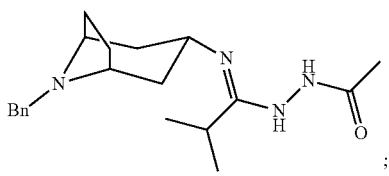

(V)

and
cyclizing the intermediate compound represented by formula (V) to obtain an intermediate compound represented by formula (VI) below,

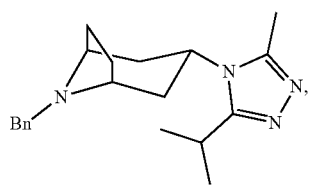

(VI)

wherein the chlorination agent is SOCl$_2$.

2. The method of claim 1, wherein the intermediate compound represented by formula (IV) is obtained by acetylating an intermediate compound represented by formula (III) below,

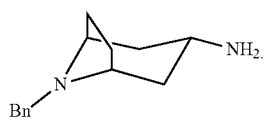

(III)

3. The method of claim 1, further comprising debenzylating the intermediate compound represented by formula (VI) by hydrogenation to obtain an intermediate compound represented by formula (II) below,

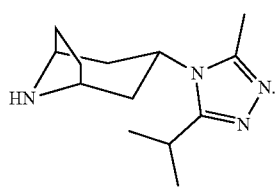

(II)

4. The method of claim 3, further comprising reacting the intermediate compound represented by formula (II) with an intermediate compound represented by formula (I) below,

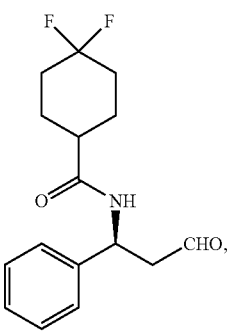

(I)

to obtain the maraviroc.

5. The method of claim 1, wherein SOCl$_2$ has an equivalent of from 1.3 to 1.7.

6. The method of claim 5, wherein the equivalent of SOCl$_2$ is around 1.5.

7. The method of claim 1, wherein reacting the intermediate compound represented by formula (IV) with the chlorination agent is carried out in the presence of a base.

8. The method of claim 7, wherein the base is a tertiary amine selected from the group consisting of triethylamine (TEA), N,N-diisopropylethylamine (DIPEA), 1,8-diazabicyclo[5.4.0]undec-7-ene (DBU), 1,4-diazabicyclo[2.2.2]octane (DABCO), 1,5-diazabicyclo[4.3.0]non-5-ene (DBN), N-methylmorpholine and pyridine.

9. The method of claim 8, wherein the base is pyridine.

10. The method of claim 9, wherein the pyridine has an equivalent of from 2.2 to 8.8.

11. The method of claim 10, wherein the equivalent of pyridine is around 4.4.

12. The method of claim 7, wherein reacting the intermediate compound represented by formula (IV) with the chlorination agent is carried out at a temperature in a range from −10° C. to 25° C.

13. The method of claim 12, wherein the temperature is in a range from 0° C. to 5° C.

14. The method of claim 7, wherein reacting the intermediate compound represented by formula (IV) with the chlorination agent is carried out in the presence of an aprotic solvent.

15. The method of claim 14, wherein the aprotic solvent is selected from the group consisting of dichloromethane, acetonitrile, tetrahydrofuran, ethyl acetate and dimethyl formamide.

16. The method of claim 15, wherein the aprotic solvent is acetonitrile.

17. The method of claim 14, wherein a weight ratio of the intermediate compound represented by formula (IV) to the aprotic solvent is from 1:4 to 1:12.

18. The method of claim 17, wherein the weight ratio of the intermediate compound represented by formula (IV) to the aprotic solvent is about 1:8.

* * * * *